(12) United States Patent
Raab et al.

(10) Patent No.: US 9,533,104 B2
(45) Date of Patent: Jan. 3, 2017

(54) ASSEMBLY FOR A DRUG DELIVERY DEVICE AND PISTON ROD

(75) Inventors: Steffen Raab, Frankfurt am Main (DE); Sandra Arnhold, Frankfurt am Main (DE)

(73) Assignee: Sanofi-Aventis Deutshcland GmbH, Frankfurt am Main (DE)

( * ) Notice: Subject to any disclaimer, the term of this patent is extended or adjusted under 35 U.S.C. 154(b) by 753 days.

(21) Appl. No.: 13/884,210

(22) PCT Filed: Nov. 11, 2011

(86) PCT No.: PCT/EP2011/069958
§ 371 (c)(1),
(2), (4) Date: May 8, 2013

(87) PCT Pub. No.: WO2012/062909
PCT Pub. Date: May 18, 2012

(65) Prior Publication Data
US 2013/0226097 A1    Aug. 29, 2013

(30) Foreign Application Priority Data

Nov. 12, 2010    (EP) .................................... 10190938

(51) Int. Cl.
*A61M 5/315*    (2006.01)

(52) U.S. Cl.
CPC ....... *A61M 5/31548* (2013.01); *A61M 5/3158* (2013.01); *A61M 5/31555* (2013.01); *A61M 5/31593* (2013.01); *A61M 5/3156* (2013.01)

(58) Field of Classification Search
CPC ..................... A61M 5/31555; A61M 5/31548; A61M 5/31593; A61M 5/3158; A61M 5/3156
See application file for complete search history.

(56) References Cited

U.S. PATENT DOCUMENTS

| 8,905,975 B2 | 12/2014 | Perot |
| 2006/0258989 A1* | 11/2006 | Kirchhofer .................. 604/207 |
| 2010/0137792 A1 | 6/2010 | Boyd et al. |

FOREIGN PATENT DOCUMENTS

| DE | 102006004562 A1 | 7/2007 |
| EP | 1923083 A1 | 5/2008 |

(Continued)

OTHER PUBLICATIONS

English Translation of Abstract of Japanese Patent Application No. JP4256758 issued Apr. 22, 2009.

*Primary Examiner* — Nathan R Price
*Assistant Examiner* — Melissa A Snyder
(74) *Attorney, Agent, or Firm* — McDonnell Boehnen Hulbert & Berghoff LLP

(57) ABSTRACT

An assembly for a drug delivery device comprises a drive member which is adapted and arranged to be displaced in a dose setting direction for setting a dose of a drug and to be displaced in a dose delivery direction for delivering the set dose of the drug. The assembly comprises a piston rod which is adapted and arranged to be displaced in the dose delivery direction via mechanical interaction with the drive member for delivering the set dose. The assembly comprises at least one resilient pre-delivery element, wherein the assembly is configured such that the resilient pre-delivery element is biased when the drive member is displaced in the dose setting direction for setting the dose, the biased resilient pre-delivery element relaxes before the drive member is displaced in the dose delivery direction for delivering the dose. When the resilient pre-delivery element relaxes, the piston rod is displaced with respect to the resilient pre-delivery element in the dose delivery direction by a pre-delivery distance. Furthermore, a piston rod is provided.

17 Claims, 3 Drawing Sheets

(56) References Cited

FOREIGN PATENT DOCUMENTS

| | | | |
|---|---|---|---|
| FR | 2905682 | A1 | 3/2008 |
| JP | 4265758 | B2 | 4/2009 |
| JP | 2010503447 | A | 2/2010 |
| WO | 03020347 | A2 | 3/2003 |
| WO | 2009092807 | A1 | 7/2009 |
| WO | 2010063707 | A1 | 6/2010 |

* cited by examiner

ASSEMBLY FOR A DRUG DELIVERY DEVICE AND PISTON ROD

CROSS REFERENCE TO RELATED APPLICATIONS

The present application is a U.S. National Phase Application pursuant to 35 U.S.C. §371 of International Application No. PCT/EP2011/069958 filed Nov. 11, 2011, which claims priority to European Patent Application No. 10190938.0 filed Nov. 12, 2010. The entire disclosure contents of these applications are herewith incorporated by reference into the present application.

FIELD OF INVENTION

This disclosure relates to an assembly for a drug delivery device. The disclosure further relates to a piston rod suitable for use in a drug delivery device.

BACKGROUND

In a drug delivery device, often, a bung within a cartridge containing a plurality of doses of a drug is displaced by a piston rod. Thereby, a dose of the drug is expelled from the cartridge.

A drug delivery device is described in document EP 1 923 083 A1, for example.n.

SUMMARY

It is an object of the present disclosure to provide an assembly facilitating provision of an improved drug delivery device, for example a device having high dose accuracy. Furthermore, a piston rod should be provided which is suitable to be integrated in an improved drug delivery device.

This object may be achieved by the subject matter of the independent claims. Further features are the subject matter of the dependent claims.

One aspect relates to an assembly for a drug delivery device. The assembly may comprise a drive member. The drive member may be configured to be displaced in a dose setting direction for setting a dose of a drug. The drive member may be configured to be displaced in a dose delivery direction for delivering the set dose of the drug. The assembly may comprise a piston rod. The piston rod may be adapted and arranged to be displaced in the dose delivery direction via mechanical interaction, e.g. engagement, with the drive member for delivering the set dose. The piston rod may be a gear rod, for example. The assembly may comprise at least one resilient pre-delivery element. The assembly is expediently configured such that the resilient pre-delivery element is biased when the drive member is displaced in the dose setting direction for setting the dose, in particular during the movement of the drive member. The biased resilient pre-delivery element may relax before the drive member is displaced in the dose delivery direction for delivering the dose. The assembly may be configured to permit that the resilient pre-delivery element relaxes before the drive member is moved in the dose delivery direction. When the resilient pre-delivery element relaxes, the piston rod may be displaced with respect to the resilient pre-delivery element in the dose delivery direction by a pre-delivery distance.

The assembly may comprise a housing having distal end and a proximal end. The dose delivery direction may be the distal direction with respect to the housing. The dose setting direction may be the proximal direction with respect to the housing.

The assembly may further comprise a cartridge holding a plurality of doses of a drug. A bung may be retained in the cartridge. In an initial state, there may be a gap between the piston rod, in particular the distal end of the piston rod, and the bung, in particular the proximal end of the bung. Said gap may arise from manufacturing tolerances. Preferably, the pre-delivery distance by which the piston rod is displaced in the dose delivery direction before delivering the set dose is equal to or greater than the size of said gap. Accordingly, due to displacement of the piston rod by the pre-delivery distance, the gap may be automatically minimized, preferably removed, before a dose delivery operation takes place. In particular, after the piston rod was displaced by the pre-delivery distance, the piston rod may abut the bung. In this way, provision of a drug delivery device having high dose accuracy is facilitated. Underdosing, which may have fatal or lethal consequences for the user may be prevented. User-operated steps, e.g. a priming step, for minimizing the gap between the piston rod and the bung may be redundant.

According to an embodiment, the drive member and the resilient pre-delivery element are adapted and arranged to be displaced in the dose setting direction with respect to the piston rod for setting the dose. The drive member, the resilient pre-delivery element and the piston rod may be adapted and arranged to be displaced together in the dose delivery direction for delivering the set dose.

Movement of the drive member in the dose delivery direction may be automatically transferred into movement of the piston rod in the dose delivery direction for delivering the set dose. Movement of the piston rod in the dose setting direction away from the bung, which would increase the gap between the bung and the piston rod, may be prevented due to mechanical interaction of the piston rod and the housing. Thus, provision of a device having high dose accuracy may be facilitated.

According to an embodiment, the resilient pre-delivery element is part of the drive member.

Accordingly, provision of a compact drug delivery device comprising a small number of components and, hence, being less prone to errors may be facilitated.

According to an embodiment, the piston rod comprises at least one, preferably two or more, pre-delivery elevations. The respective pre-delivery elevation may comprise a biasing section, e.g. a distal section. The pre-delivery elevation may comprise a pre-delivery section, e.g. a proximal proximal section. The resilient pre-delivery element may be configured to mechanically interact with the biasing section when the drive member is displaced in the dose setting direction with respect to the piston rod, e.g. during the dose setting operation. The resilient pre-delivery element may be biased when mechanically interacting with the biasing section. The resilient pre-delivery element may be adapted and arranged to relax during mechanical interaction with the pre-delivery section. The resilient pre-delivery element may be configured to transfer force to the piston rod during relaxation. In this way, the piston rod may be displaced by the pre-delivery distance in the dose delivery direction.

The piston rod may be displaced by the pre-delivery distance in the dose delivery direction before displacing the drive member and, hence, the piston rod, in the dose delivery direction for delivering the set dose, e.g. before the dose delivery operation takes place. In particular, displacement of the piston rod by the pre-delivery distance may occur in connection with the dose setting operation. Hence, any gap between the piston rod and the bung may be closed before the set dose is delivered. In particular, said gap may be closed before the needle is inserted into the tissue.

According to an embodiment, the piston rod comprises a plurality of pre-delivery elevations. Each pre-delivery elevation may comprise a biasing section and a pre-delivery section.

The number of pre-delivery elevations may correspond to the number of doses held in the cartridge, for example. Displacement of the piston rod by the pre-delivery distance may thus occur repeatedly, for example in connection with each dose setting operation.

According to an embodiment, the pre-delivery distance is less than the displacement of the piston rod in the dose delivery direction for delivering the set dose of the drug.

The pre-delivery distance may be adapted to the size of the dose to be dispensed and/or to the average size of the gap between the bung and the piston rod. Waste of the drug, which may arise from a too large pre-delivery distance by which the piston rod is displaced, may be prevented in this way.

According to an embodiment, the assembly comprises at least one displacement element. The displacement element may be adapted and arranged to be displaced together with the resilient pre-delivery element in the dose setting direction when the drive member is displaced in the dose setting direction. The displacement element may be adapted and arranged to be displaced together with the resilient pre-delivery element in the dose delivery direction when displacing the drive member in the dose delivery direction. Displacement of the piston rod with respect to the drive member in the dose delivery direction by the pre-delivery distance may put the displacement element in a displacement position. In the displacement position, the displacement element may interact with the displacement elevation when the drive member is displaced in the dose delivery direction. The displacement position may be a dose delivery position. In particular, in the displacement position, the displacement element may be configured to mechanically interact with the piston rod such that the piston rod is displaceable together with the drive member in the dose delivery direction for delivering the set dose of the drug.

In particular, due to displacement of the piston rod by the pre-delivery distance, the displacement element may be enabled to interact with the piston rod, i.e. it may be put into the displacement position, such that common displacement of the drive member and the piston rod for delivering the set dose of the drug is enabled.

According to an embodiment, the displacement element may be part of the drive member. In particular, the drive member and the displacement element may be formed unitarily. Thus, provision of a compact drug delivery device comprising a small number of components and, hence, a drug delivery device being less prone to errors is facilitated.

According to an embodiment, the piston rod comprises at least one, preferably two or more, displacement elevations. The respective displacement elevation may be arranged opposite to the pre-delivery elevation with respect to the main longitudinal axis of the piston rod. The displacement elevation may comprise a dose setting section, e.g. a distal section. The dose setting section may be adapted and arranged to mechanically interact with the displacement element when the drive member is displaced in the dose setting direction. The displacement elevation may comprise a displacement section, e.g. a proximal section. The displacement section may be adapted and arranged to mechanically cooperate with the displacement element when the drive member is displaced in the dose delivery direction. The pre-delivery section of the pre-delivery elevation may be oblique with respect to the main longitudinal axis of the piston rod. The displacement section of the displacement elevation may be less oblique than the pre-delivery section.

The oblique shape of the pre-delivery section may facilitate interaction of the piston rod, in particular of the pre-delivery section, with the resilient pre-delivery element for effectively displacing the piston rod by the pre-delivery distance. The less oblique shape of the displacement section may help preventing mechanical interaction of the piston rod, in particular of the displacement section, and the displacement element before the piston rod was displaced by the pre-delivery distance. Movement of the piston rod before dose delivery is commenced may be prevented in this way.

The number of displacement elevations may correspond to the number of doses held in the cartridge, for example. In this way, provision of a re-usable drug delivery device, i.e. a drug delivery device enabling dispensing of a plurality of doses of the drug, may be facilitated.

According to an embodiment, the pre-delivery distance is determined by the length of the projection of the pre-delivery section of the pre-delivery elevation onto the main longitudinal axis of the piston rod.

By varying the length of the projection, the pre-delivery distance may be adaptable to the size of the dose to be dispensed and/or the average size of the gap between the piston rod and the bung.

According to an embodiment, the drive member is arranged within the piston rod. The pre-delivery elevation and the displacement elevation may be arranged within and, in particular, along an inner surface of the piston rod.

In this way, provision of a space-saving drug delivery device may be facilitated.

A further aspect relates to a piston rod for a drug delivery device. The piston rod may be a gear rod. The gear rod may comprise a first set of teeth. The previously mentioned pre-delivery elevations may correspond to the first set of teeth. The gear rod may comprise a second set of teeth. The previously mentioned displacement elevations may correspond to the second set of teeth. An axial position with respect to the piston rod of one tooth of the first set may correspond to the axial position with respect to the piston rod of one tooth of the second set. The teeth of the first set may comprise a shape which is different from the shape of the teeth of the second set. The teeth of one respective set may have an equal shape.

The different shapes may facilitate interaction of the piston rod with a drive mechanism, e.g. the previously described drive member, of the device. In particular, the different shapes may allow an automatic priming of the device before a dose delivery operation takes place. The same axial position of the teeth of the first and second sets may ensure that immediately after the automatic priming was performed, a dose delivery operation can take place.

According to an embodiment, the piston rod comprises a distal end. The piston rod may comprise a proximal end. One respective tooth of the first set may comprise a distal section. The distal section may face the distal end of the piston rod. The respective tooth of the first set may comprise a proximal section. The proximal section may face away from the distal end of the piston rod. One respective tooth of the second set may comprise a distal section. Said distal section may face the distal end of the piston rod. The respective tooth of the second set may comprise a proximal section. The proximal section may face away from the distal end of the piston rod.

The proximal section of the respective tooth of the first set may be oblique with respect to the main longitudinal axis of the piston rod. The proximal section of the respective tooth of the second set may be less oblique than the proximal section of the tooth of the first set.

Said arrangement may enable interaction of the previously described displacement member with the proximal section of one respective tooth of the second set only after interaction of the previously described resilient pre-delivery element with the proximal section of one respective tooth of the first set during the dose setting operation was performed. Accordingly, displacement of the piston rod for delivering the set dose may be prevented unless the piston rod was displaced by the pre-delivery distance.

According to an embodiment, the proximal section of the respective tooth of the first set of teeth is terminated by a first proximal edge. The proximal section of the respective tooth of the second set of teeth may be terminated by a second proximal edge. The first proximal edge may be arranged closer to the distal end of the piston rod than the second proximal edge.

In this way, mechanical interaction of the resilient pre-delivery element with the proximal section of the respective tooth of the first set during a dose setting operation may take place prior to mechanical interaction of the displacement element with the proximal section of the respective tooth of the second set.

According to an embodiment, the first set of teeth and the second set of teeth are arranged inside the piston rod.

According to an embodiment, the first set of teeth and the second set of teeth are arranged on a common surface, particularly on an inner surface, of the piston rod.

In this way, provision of a compact piston rod may be facilitated.

A further aspect relates to a drug delivery device. The device may comprise the previously described assembly. The device may be a fixed dose device, in particular a pen-type fixed dose drug delivery device.

A further aspect relates to a piston rod for a drug delivery device. The piston rod may comprise a distal end. The piston rod may comprise a proximal end. The piston rod may comprise a main longitudinal axis. The piston rod may comprise one tooth having an oblique section. The oblique section may face away from the distal end of the piston rod. The length of the projection of the oblique section onto the main longitudinal axis of the piston rod may determine a distance by which the piston rod is displaceable.

According to a preferred embodiment, an assembly for a drug delivery device is provided, the assembly comprising a drive member which is adapted and arranged to be displaced in a dose setting direction for setting a dose of a drug and to be displaced in a dose delivery direction for delivering the set dose of the drug. The assembly comprises a piston rod which is adapted and arranged to be displaced in the dose delivery direction via mechanical interaction with the drive member for delivering the set dose. The assembly comprises at least one resilient pre-delivery element, wherein the assembly is configured such that the resilient pre-delivery element is biased when the drive member is displaced in the dose setting direction for setting the dose, the biased resilient pre-delivery element relaxes before the drive member is displaced in the dose delivery direction for delivering the dose. When the resilient pre-delivery element relaxes, the piston rod is displaced with respect to the resilient pre-delivery element in the dose delivery direction by a pre-delivery distance.

Due to displacement of the piston rod in the dose delivery direction by the pre-delivery distance, a potential gap between the piston rod and a bung of a cartridge in a drug delivery device comprising the assembly may be closed automatically. Dose accuracy may be increased in this way.

According to a preferred embodiment, a piston rod for a drug delivery device is provided, wherein the piston rod is a gear rod. The gear rod comprises a first set of teeth and a second set of teeth. An axial position with respect to the piston rod of one tooth of the first set corresponds to the axial position with respect to the piston rod of one tooth of the second set. The teeth of the first set comprise a shape which is different from the shape of the teeth of the second set.

The different shape of the teeth may facilitate interaction of the piston rod with a drive mechanism of the drug delivery device. In particular, the different shapes may enable an automatic priming step for a drug delivery device comprising the piston rod.

Of course, features described above in connection with different aspects and embodiments may be combined with each other and with features described below.

BRIEF DESCRIPTION OF THE DRAWINGS

Further features and refinements become apparent from the following description of the exemplary embodiments in connection with the accompanying figures.

DETAILED DESCRIPTION

Figure 1:
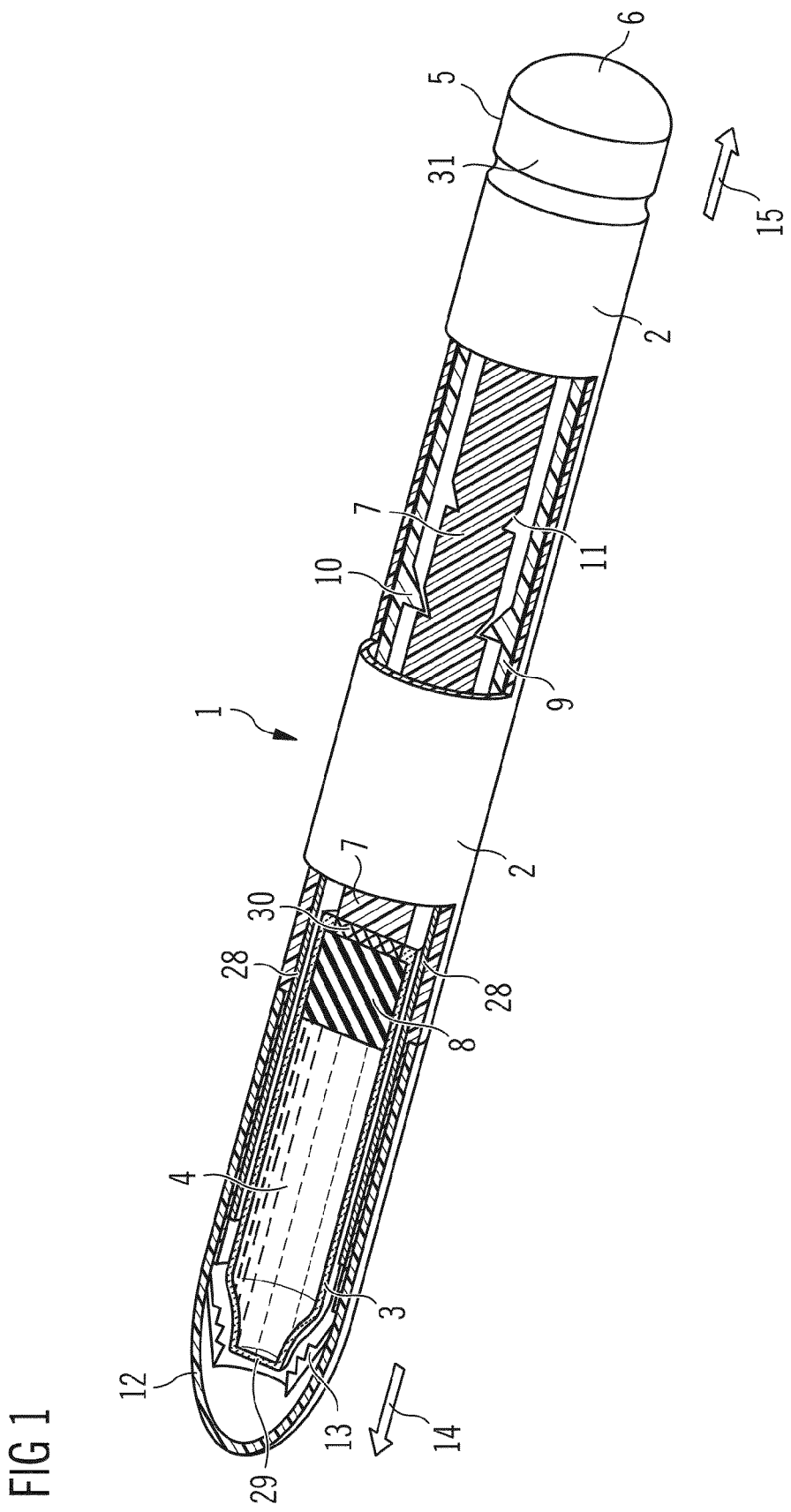
FIG. 1 schematically shows a perspective sectional view of an exemplary drug delivery device, FIG. 2 schematically shows a sectional side view of an assembly for a drug delivery device, and FIG. 3 schematically shows a sectional side view of the assembly of FIG. 2.

Like elements, elements of the same kind and identically acting elements may be provided with the same reference numerals in the figures.

In FIG. 1 a drug delivery device 1 is shown. The drug delivery device 1 comprises a housing 2. The drug delivery device 1 and the housing 2 have a distal end and a proximal end. The distal end is indicated by arrow 14. The proximal end is indicated by arrow 15. The term "distal end" designates that end of the drug delivery device 1 or a component thereof which is or is to be arranged closest to a dispensing end of the drug delivery device 1. The term "proximal end" designates that end of the device 1 or a component thereof which is or is to be arranged furthest away from the dispensing end of the device 1. The distal end and the proximal end are spaced apart from one another in the direction of an axis. The axis may be the main longitudinal axis of the device 1.

The drug delivery device 1 comprises a cartridge 3. The cartridge 3 is permanently or releasably retained within a cartridge holder 28. The cartridge holder 28 stabilizes the cartridge 3 mechanically. The cartridge holder 28 may be, permanently or releasably, attached, preferably glued or screwed, to the housing 2 of the drug delivery device 1.

The cartridge 3 contains a drug 4, preferably a plurality of doses of the drug 4.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group -Lys6-NH2 may be bound to the C-terminus of the Exendin-4
derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2, \
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-H2,
H-Asn-(Glu)5-des Pro36, Pro37, Pro38 [Met(O)14, Trp (O2)25, Asp28] Exendin-4(1-39)-Lys)6-NH2;
or a pharmaceutically acceptable salt or solvate of any one of the aforementioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The cartridge 4 has an outlet 29. The outlet 29 may be covered by a membrane. For delivery of the drug 4, the membrane may be penetrated, for example pierced, e.g. by a needle assembly (not explicitly shown). The drug delivery device 1 comprises engaging means 13, preferably for attaching the needle assembly to the cartridge holder 28.

The drug delivery device 1 comprises a piston rod 7. The piston rod 7 has a distal and a proximal end. The distal end of the piston rod 7 may be the end which is closest to the distal end 14 of the drug delivery device 1 when the piston rod 7 has been introduced in the device 1. The proximal end of the piston rod 7 may be the end which is furthest away from the distal end 14 of the drug delivery device 1 when the piston rod 7 has been introduced in the device 1.

The piston rod 7 may operate through the housing 2 of the drug delivery device 1. The piston rod 7 may be designed to transfer axial movement through the drug delivery device 1, for example for the purpose of delivering the drug 4. The piston rod 7 may be configured to be axially displaced in a dose delivery direction for delivering a dose of the drug 4. The dose delivery direction may be the distal direction with respect to the housing 2. Preferably, the piston rod 7 is prevented from being axially displaced in a dose setting direction when setting a dose of the drug 4. The dose setting direction may be the proximal direction with respect to the housing 2. Preferably, the piston rod 7 is prevented from being rotated with respect to the housing 2 when setting and when delivering a dose of the drug 4.

The piston rod 7 may be a gear rod, a lead-screw, a rack or the like. The piston rod 7 may be made of a flexible or a rigid material. The piston rod 7 may have a circular or a non-circular cross-section. The piston rod 7 may be of unitary or multipart construction. A bearing member 30 may be located at the distal end of the piston rod 7. The bearing member 30 may facilitate interaction of the piston rod 7 with a bung 8.

The bung 8 is slideably retained within the cartridge 3 of the drug delivery device 1. The bung 8 seals the cartridge 3 proximally. Movement of the bung 8 in the distal direction with respect to the cartridge 3 causes the drug 4 to be dispensed from the cartridge 3 through the outlet 29.

In an initial state of the device 1, e.g. the state of the device 1 as originally supplied from the manufacturer, there may be a gap between the bung 8 and the piston rod 7. Said gap may be due to manufacturing tolerances. For guaranteeing high dose accuracy and, hence, for preventing underdosing said gap has to be minimized, preferably removed, e.g. a priming step has to be performed, before dispensing a set dose of the drug 4 from the cartridge 3. Said priming is explained in more detail in connection with FIGS. 2 and 3.

The device 1 comprises an inner sleeve 9. The inner sleeve 9 may be an insert sleeve within the housing 2. Preferably, the inner sleeve 9 is secured against rotational and translatory movement with respect to the housing 2. The inner sleeve 9 comprises stop members 10. The stop members 10 extend along a main longitudinal axis of the inner sleeve 9. For clarity reasons, only two stop members 10 are shown in FIG. 1. However, the inner sleeve 9 may comprise a plurality of stop members 10. The stop members 10 may comprise a protrusion.

The piston rod 7 comprises a set of piston rod stop members 11. The stop members 10 of the inner sleeve 9 may be configured to mechanically cooperate, in particular to engage, with the piston rod stop members 11 to prevent movement of the piston rod 7 in the dose setting direction, e.g. in the proximal direction, with respect to the housing 2, when setting a dose of the drug 4. For clarity reasons, only four piston rod stop members 11 are shown in FIG. 1. However, the piston rod 7 may comprise a plurality of piston rod stop members 11. In particular, the number of piston rod stop members 11 may correspond to the number of doses held in the cartridge 3.

The piston rod stop members 11 extend longitudinally along an outer surface of the piston rod 7. The piston rod stop members 11 may be arranged equidistantly as shown in FIG. 1. A pair of piston rod stop members 11 may be arranged oppositely with respect to the main longitudinal axis of the piston rod 7. The piston rod stop members 11 may comprise an indentation, for example.

Figure 2:
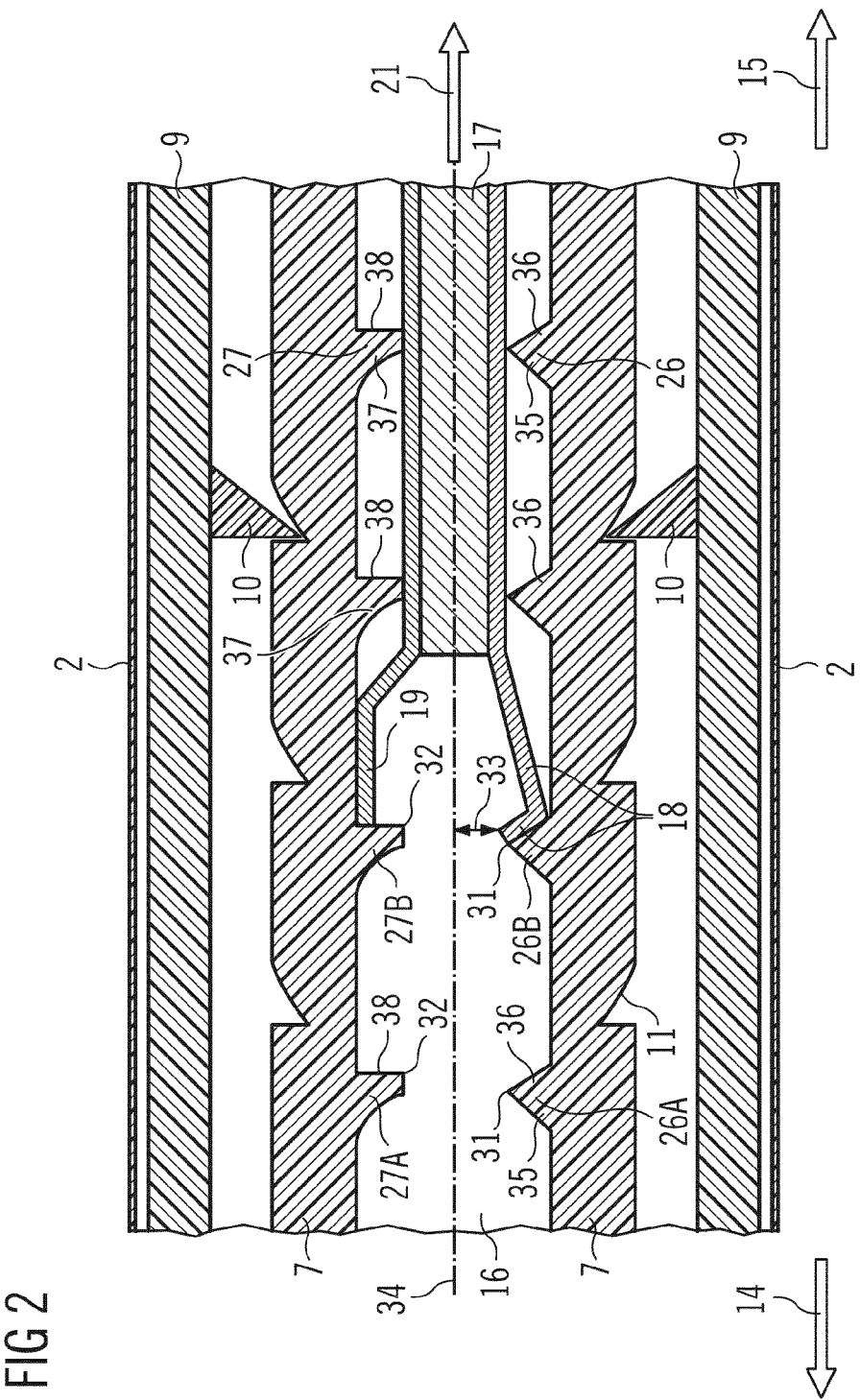
Figure 3:
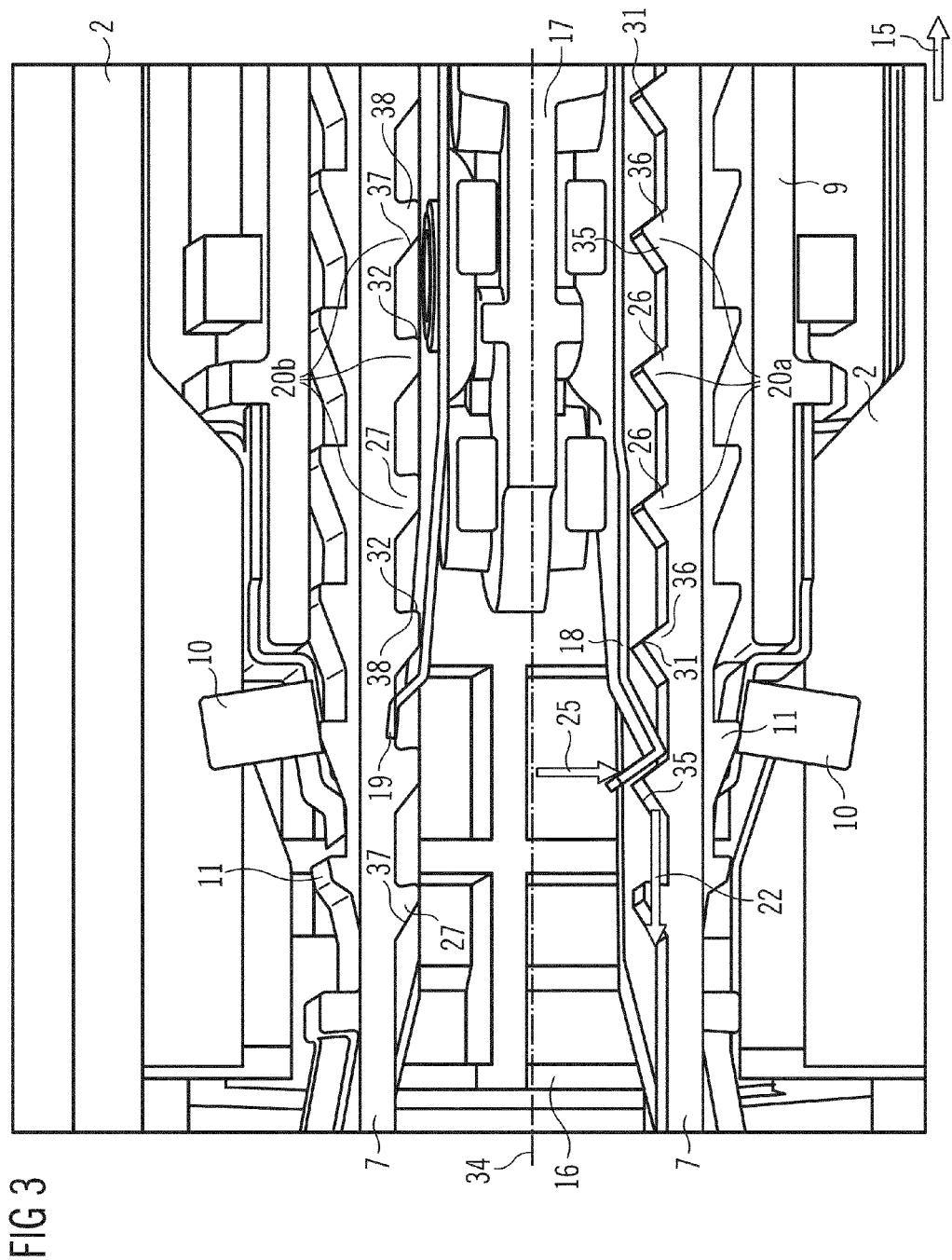

The drug delivery device 1 comprises a drive member (see drive member 17 in FIGS. 2 and 3). The drive member 17 is arranged inside the piston rod 7. The drive member 17 is configured to be displaced in the dose setting direction, with respect to the housing 2 for setting the dose of the drug 4. The drive member 17 is configured to be displaced with respect to the piston rod 7 when setting the dose of the drug 4. The drive member 17 is configured to be displaced in the dose delivery direction with respect to the housing 2 for delivering the dose of the drug 4. When delivering the dose, movement of the drive member 17 in the distal direction with respect to the housing 2 is transferred into movement of the piston rod 7 in the distal direction with respect to the housing 2.

The drug delivery device 1 comprises a dose member 5. The drug delivery device 1 comprises a dose button 6. The dose button 6 may be integrally formed with the dose member 5 or may be connected to the dose member 5. In the latter case the dose button 6 may be secured to the dose member 5, in particular secured against rotational movement with respect to the dose member 5.

The dose member 5 is provided with a grip surface 31. A user may grip the grip surface 31 for moving the dose member 5 with respect to the housing 2 for setting a dose of the drug 4. Operation of setting and delivering a dose of the drug 4 is described in connection with the description of FIG. 2 in more detail.

The drug delivery device 1 may be a pen-type device, in particular a pen-type injector. The device 1 may be a disposable or a re-usable device and may be configured to dispense fixed doses of the drug 4, e.g. doses the size of which may not be varied by the user. The drug delivery device 1 may be a manually, in particular a non-electrically, driven device.

FIG. 2 schematically shows a sectional side view of an assembly for a drug delivery device. In particular, FIG. 2 shows the piston rod 7 and the drive member 17 at the end of a dose setting operation.

Preferably, the piston rod 7 is a gear rod. The piston rod 7 comprises a plurality of pre-delivery elevations 26, e.g. teeth. The pre-delivery elevations 26 have a biasing section 35. The pre-delivery elevations 26 have a pre-delivery section 36. The pre-delivery elevations 26 may form a set of pre-delivery teeth 20a, i.e. a first set of teeth, of the piston rod 7. The pre-delivery section 36 is arranged further away from the distal end of the piston rod 7 than the biasing section 35. In particular, the pre-delivery section 36 faces away from the distal end of the piston rod 7.

The piston rod 7 comprises a plurality of displacement elevations 27, e.g. teeth. The displacement elevations 27 have a dose setting section 37. The displacement elevations 27 have a displacement section 38. The displacement elevations 27 form a set of displacement teeth 20b, i.e. a second set of teeth, of the piston rod 7. The displacement section 38 is arranged further away from the distal end of the piston rod 7 than the dose setting section 37. In particular, the displacement section 38 faces away from the distal end of the piston rod 7.

The pre-delivery elevations 26 are arranged along the main longitudinal axis 34 of the piston rod 7. The displacement elevations 27 are arranged along the main longitudinal axis 34 of the piston rod 7. Preferably, the pre-delivery elevations 26 and the displacement elevations 27 are arranged at a common surface, e.g. the inner surface, of the piston rod 7. Preferably, the pre-delivery elevations 26 and the displacement elevations 27 are arranged inside the piston rod 7. The pre-delivery elevations 26 are arranged at equidistant intervals. The displacement elevations 27 are arranged at equidistant intervals. This may help enabling provision of a fixed dose drug delivery device 1, for example.

One pre-delivery elevation 26 may be assigned to one corresponding displacement elevation 27. In particular, the axial position of one respective pre-delivery elevation 26 with respect to the main longitudinal axis 34 of the piston rod 7 corresponds to the axial position of a corresponding displacement elevation 27 with respect to the main longitudinal axis 34 of the piston rod 7.

The pre-delivery section 36 comprises a pre-delivery edge 31. The pre-delivery edge 31 terminates the pre-delivery section 36. In particular, the pre-delivery edge 31 separates the pre-delivery section 36 from the biasing section 35. The displacement section 38 comprises a displacement edge 32. The displacement edge 32 terminates the displacement section 38. In particular, displacement edge 32 separates the displacement section 38 from the dose setting section 37. Pre-delivery edge 31 is arranged closer to the distal end of the piston rod 7 than displacement edge 32.

The pre-delivery elevations 26 comprise a shape which is different from the shape of the displacement elevations 27. In particular, the pre-delivery section 36 is oblique with respect to the main longitudinal axis 34 of the piston rod 7. The displacement section 38 is less oblique than the pre-delivery section 36. Said embodiment of the pre-delivery elevations 26 and the displacement elevations 27 may facilitate interaction of the piston rod 7 with the drive member 17 as explained later on in more detail.

The drug delivery device 1 comprises a resilient pre-delivery element 18. The resilient pre-delivery element 18 may be a resilient arm, for example. The device 1 comprises a displacement element 19. The displacement element 19 may be a resilient arm, for example. The pre-delivery element 18 and the displacement element 19 may comprise differently formed resilient arms.

The pre-delivery element 18 is configured to interact with the pre-delivery elevations 26 of the piston rod 7. The displacement element 19 is configured to interact with the displacement elevations 27 of the piston rod 7.

The resilient pre-delivery element 18 and the displacement element 19 are configured to be displaced together in the dose setting direction when displacing the drive member 17 in the dose setting direction, i.e. when setting a dose. The resilient pre-delivery element 18 and the displacement element 19 are configured to be displaced together in the dose delivery direction when displacing the drive member 17 in the dose delivery direction, i.e. when delivering the set dose. When setting the dose the resilient pre-delivery element 18 and the displacement element 19 may be displaced with respect to the piston rod 7. When delivering the dose the resilient pre-delivery element 18, the displacement element 19, the drive member 17 and the piston rod 7 may be displaced together.

The resilient pre-delivery element 18 and the displacement element 19 may be part of the drive member 17, as shown in FIG. 2, or may be separate members. The resilient pre-delivery element 18 and the displacement element 19 are arranged in the distal end section of the drive member 17.

The resilient pre-delivery element 18 is configured to be resilient in the radial direction with respect to the main longitudinal axis 34, as indicated by arrow 33. The displacement element 19 is configured to be resilient in the radial direction with respect to the main longitudinal axis 34. The pre-delivery element 18 and the displacement element 19 comprise a different shape. The pre-delivery element 18, in particular the distal end surface of the pre-delivery element 18, is oblique with respect to the main longitudinal axis of the drive member 17. The shape of the distal end of the pre-delivery element 18 may be adapted to the shape of the pre-delivery section 36 of the pre-delivery elevation 26. The displacement element 19, in particular the distal end surface of the displacement element 19, is less oblique with respect to the main longitudinal axis of the drive member 17 than the pre-delivery element 18. The shape of the distal end surface of the displacement element 19 may be adapted to the shape of the displacement section 38 of the displacement elevation 27.

Before setting a dose of the drug 4 the resilient pre-delivery element 18 and the displacement element 19 may be arranged in a starting position which is in the following referred to as "position A". In position A the distal end of the resilient pre-delivery element 18 may abut the pre-delivery section 36 of a first pre-delivery elevation 26A. In position A, the distal end of the displacement element 19 may abut the displacement section 38 of a first displacement elevation 27A.

When setting a dose of the drug 4, the user grips the grip surface 31. The user will then pull the dose member 5 in the proximal direction with respect to the piston rod 7. Proximal movement of the dose member 5 causes the drive member 17 to be displaced axially in the proximal direction with respect to the piston rod 7, which is indicated by arrow 21. Proximal displacement of the piston rod 7 is prevented when displacing the drive member 17 in the proximal direction due to mechanical cooperation of the stop members 10 with the piston rod stop members 11, as described previously.

The resilient pre-delivery element 18 and the displacement element 19 are displaced together with the drive member 17 in the proximal direction with respect to the piston rod 7. Thereby, the resilient pre-delivery element 18 slides along the biasing section 35 of a second pre-delivery elevation 26B. The second pre-delivery elevation 26B is arranged further away from the distal end of the piston rod 7 than the first pre-delivery elevation 26A. In particular, the second pre-delivery elevation 26B succeeds the first pre-delivery elevation 26A in the proximal direction with respect to the housing 2.

When sliding along the biasing section 35 the resilient pre-delivery element 18 is biased, e.g. it may be bowed radially inwardly with respect to the housing 2 (see upper part of arrow 33). While the resilient pre-delivery element 18 slides along the biasing section 35 the displacement element 19 is displaced in the proximal direction with respect to the housing 2, thereby interacting with the dose setting section 37 of a second displacement elevation 27B. While interacting with the dose setting section 37, the displacement element 19 is bowed radially inwardly with respect to the housing 2.

While displacing the drive member 17 further in the dose setting direction, the resilient pre-delivery element 18 passes the pre-delivery edge 31, afterwards sliding down the pre-delivery section 36 of the second pre-delivery elevation 26B. Thereby, the pre-delivery element 18 relaxes. The resilient pre-delivery element 18 relaxes radially outwardly with respect to the housing 2 (see "down-part" of arrow 33 and arrow 25, FIG. 3). Hence, the pre-delivery element 18 transfers a radially outwardly directed force, in particular the spring force stored while sliding up the biasing section 35, to the piston rod 7. Said force causes the piston rod 7 to be axially displaced by a pre-delivery distance in the dose delivery direction (see arrow 22, FIG. 3), e.g. towards the bung 8. This is herein also referred to as automatic priming of the device 1.

The automatic priming of the device 1 minimizes, preferably removes, the gap between the piston rod 7 and the bung 8 before delivering the dose, hence ensuring a high dose accuracy of the drug delivery device 1. In particular, the priming may help to prevent dispensing of underdoses, which may have fatal or lethal consequences for the user. As the priming occurs automatically at the end of a dose setting operation, user-operated steps for minimizing the gap between the piston rod 7 and the bung 8 may be redundant. Hence, the drug delivery device 1 is an easily handled and user-friendly device providing high safety for the user.

The resilient pre-delivery element 18 is configured to be biased and to relax while interacting with the same pre-delivery elevation 26, e.g. pre-delivery elevation 26B. The biased resilient pre-delivery element 18 may relax before displacing the drive member 17 in the dose delivery direction for delivering the set dose.

The pre-delivery distance may be less than the displacement of the piston rod 7 in the dose delivery direction for delivering the set dose of the drug 4. The displacement of the piston rod 7 in the dose delivery direction for delivering the set dose of the drug 4 may characterize the size of the dose dispensed. In particular, the pre-delivery distance may be less than the smallest dose increment.

The distance between the pre-delivery edge 31 of the pre-delivery section 36 and the end of the pre-delivery section 36, in particular the length of the projection of the length of the pre-delivery section 36 onto the main longitudinal axis 34 of the piston rod 7, may determine the pre-delivery distance. A longer pre-delivery section 36 may hence involve a larger pre-delivery distance, causing the piston rod 7 to be displaced by a larger distance in the distal direction with respect to the housing 2 before the dose is being delivered. In this way, the pre-delivery distance may be adaptable to the gap between the bung 8 and the piston rod 7. An upper limit of the pre-delivery distance may be determined by the tension of the resilient pre-delivery element 18.

The number of automatic priming operations during lifetime of the device 1 depends on the number of pre-delivery elevations 26. Preferably, the automatic priming of the device 1 occurs before each dose delivery operation. In this case, the number of pre-delivery elevations 26 and, thus, also the number of displacement elevations, corresponds to the number of doses held in the cartridge 3. Alternatively, the automatic priming may occur only once, e.g. before dispensing the first dose of the drug 4.

The proximal end of the second pre-delivery elevation 26B, in particular the end of the pre-delivery section 36, may be arranged with respect to the main longitudinal axis 34 of the piston rod 7 such that it is located at the same axial position as the displacement edge 32 of the displacement section 38 of the corresponding second displacement elevation 27B. Hence, during automatic priming of the device 1, the displacement element 19 passes the displacement edge 32 relaxing to be arranged proximally with respect to the displacement section 38 of the second displacement elevation 27B. Consequently, automatic priming of the device 1 may enable the displacement element 19 to interact with the displacement section 38. In particular, the automatic priming may put the displacement element 19 in a displacement position. In the displacement position the displacement element 19 is configured to interact with the piston rod 7, in particular with the displacement section 38, such that the piston rod 7 is displaceable in the dose delivery direction for delivering the set dose of the drug 4.

When the dose has been set, the resilient pre-delivery element 18 and the displacement element 19 are arranged in an end or dose delivery position which is referred to as "position B". In position B, the distal end of the resilient pre-delivery element 18 may again abut the pre-delivery section 36 of the second pre-delivery elevation 26B. At position B, the distal end of the displacement element 19 may again abut the displacement section 38 of the second displacement elevation 27B.

When the dose has been set, the user pushes onto the dose button 6. Consequently, the dose member 5 is moved axially in the distal direction with respect to the housing 2. Distal displacement of the dose member 5 causes the drive member 17 to be moved axially in the distal direction with respect to the housing 2. As the drive member 17 is releasably engaged with the piston rod 7, movement of the drive member 17 in the distal direction with respect to the housing 2 is transferred into axial movement of the piston rod 7 in the distal direction with respect to the housing 2 due to mechanical cooperation of the displacement element 19 with the piston rod 7, in particular with the displacement section 38 of the piston rod 7. Hence, the bung 8 is moved in the distal direction with respect to the housing 2 causing the previously set dose of the drug 4 to be dispensed.

Other implementations are within the scope of the following claims. Elements of different implementations may be combined to form implementations not specifically described herein.

The invention claimed is:

1. An assembly for a drug delivery device, comprising
a drive member which is adapted and arranged to be displaced in a dose setting direction for setting a dose of a drug and to be displaced in a dose delivery direction for delivering the set dose of the drug,
a piston rod which is adapted and arranged to be displaced in the dose delivery direction via mechanical interaction with the drive member for delivering the set dose,
at least one resilient pre-delivery element, wherein the assembly is configured such that the resilient pre-delivery element is biased when the drive member is displaced in the dose setting direction for setting the dose, the biased resilient pre-delivery element relaxes before the drive member is displaced in the dose delivery direction for delivering the dose, wherein, when the resilient pre-delivery element relaxes, the piston rod is displaced with respect to the resilient pre-delivery element in the dose delivery direction by a pre-delivery distance,
wherein the resilient pre-delivery element is configured to transfer a force to the piston rod during the relaxation of the resilient pre-delivery element such that the force causes the piston rod to be axially displaced by a pre-delivery distance in the dose delivery direction.

2. The assembly according to claim 1, wherein the drive member and the resilient pre-delivery element are adapted and arranged to be displaced in the dose setting direction with respect to the piston rod for setting the dose, and wherein the drive member, the resilient pre-delivery element and the piston rod are adapted and arranged to be displaced together in the dose delivery direction for delivering the set dose.

3. The assembly according to claim 1, wherein the resilient pre-delivery element is part of the drive member.

4. The assembly according to claim 1, wherein the piston rod comprises at least one pre-delivery elevation which comprises a biasing section and a pre-delivery section, wherein the resilient pre-delivery element is configured to mechanically interact with the biasing section when the drive member is displaced in the dose setting direction with respect to the piston rod, wherein the resilient pre-delivery element is biased when mechanically interacting with the biasing section and, wherein, the biased resilient pre-delivery element is adapted and arranged to relax during mechanical interaction with the pre-delivery section, the resilient pre-delivery element being configured to transfer force to the piston rod during relaxation such that the piston rod is displaced by the pre-delivery distance in the dose delivery direction.

5. The assembly according to claim 1, wherein the pre-delivery distance is less than the distance the piston rod is displaced in the dose delivery direction for delivering the set dose of the drug.

6. The assembly according to claim 1, wherein the assembly comprises at least one displacement element which is adapted and arranged to be displaced together with the resilient pre-delivery element in the dose setting direction when displacing the drive member in the dose setting direction and to be displaced together with the resilient pre-delivery element in the dose delivery direction when displacing the drive member in the dose delivery direction, wherein displacement of the piston rod with respect to the drive member in the dose delivery direction by the pre-delivery distance puts the displacement element in a displacement position, wherein when the displacement element is in the displacement position it is configured to mechanically interact with the piston rod such that the piston rod is displaceable together with the drive member in the dose delivery direction for delivering the set dose of the drug.

7. The assembly according to claim 6, wherein the displacement element is part of the drive member.

8. The assembly according to claim 6, wherein the piston rod comprises at least one displacement elevation, the displacement elevation comprising a dose setting section adapted and arranged to mechanically interact with the displacement element when the drive member is displaced in the dose setting direction and a displacement section adapted and arranged to mechanically cooperate with the displacement element when the drive member is displaced in the dose delivery direction, wherein the pre-delivery section of the pre-delivery elevation is oblique with respect to a main longitudinal axis of the piston rod, and the displacement section of the displacement elevation is less oblique than the pre-delivery section.

9. The assembly according to claim 4, wherein the pre-delivery distance is determined by the length of the projection of the pre-delivery section of the pre-delivery elevation onto the main longitudinal axis of the piston rod.

10. The assembly according to claim 4, wherein the drive member is arranged within the piston rod and, wherein the pre-delivery elevation and the displacement elevation are arranged along an inner surface of the piston rod.

11. The assembly according to claim 1, wherein the piston rod is a gear rod, the gear rod comprising a first set of teeth and a second set of teeth, wherein an axial position with respect to the piston rod of one tooth of the first set corresponds to the axial position with respect to the piston rod of one tooth of the second set, and wherein the teeth of the first set comprise a shape which is different from the shape of the teeth of the second set.

12. The assembly according to claim 11, comprising a distal end and a proximal end, wherein one respective tooth of the first set comprises a distal section which faces the distal end of piston rod and a proximal section which faces away from the distal end of the piston rod, and one respective tooth of the second set comprises a distal section which faces the distal end of the piston rod and a proximal section which faces away from the distal end of the piston rod, wherein the proximal section of the respective tooth of the first set is oblique with respect to the main longitudinal axis of the piston rod and the proximal section of the respective tooth of the second set is less oblique than the proximal section of the tooth of the first set.

13. The assembly according to claim 12, wherein the proximal section of the respective tooth of the first set is terminated by a first proximal edge and the proximal section of the respective tooth of the second set is terminated by a second proximal edge, wherein the first proximal edge is arranged closer to the distal end of the piston rod than the second proximal edge.

14. The assembly according to claim 11, wherein the first set of teeth and the second set of teeth are arranged inside the piston rod.

15. The assembly according to claim 11, wherein the first set of teeth and the second set of teeth are arranged on a common surface of the piston rod.

16. A drug delivery device comprising the assembly according to claim 1, wherein the device is a fixed dose device.

17. An assembly for a drug delivery device, comprising
- a drive member which is adapted and arranged to be displaced in a dose setting direction for setting a dose of a drug and to be displaced in a dose delivery direction for delivering the set dose of the drug,
- a piston rod which is adapted and arranged to be displaced in the dose delivery direction via mechanical interaction with the drive member for delivering the set dose,
- at least one resilient pre-delivery element, wherein the assembly is configured such that the resilient pre-delivery element is biased when the drive member is displaced in the dose setting direction for setting the dose, the biased resilient pre-delivery element relaxes before the drive member is displaced in the dose delivery direction for delivering the dose, wherein, when the resilient pre-delivery element relaxes, the piston rod is displaced with respect to the resilient pre-delivery element in the dose delivery direction by a pre-delivery distance, and
- at least one displacement element which is adapted and arranged to be displaced together with the resilient pre-delivery element in the dose setting direction when displacing the drive member in the dose setting direction and to be displaced together with the resilient pre-delivery element in the dose delivery direction when displacing the drive member in the dose delivery direction, wherein the resilient pre-delivery element and the displacement element comprise a different shape.

* * * * *